US010172826B2

(12) United States Patent
Minatelli et al.

(10) Patent No.: US 10,172,826 B2
(45) Date of Patent: Jan. 8, 2019

(54) COMPOSITION AND METHOD TO TREAT AND ALLEVIATE SYMPTOMS OF HOT FLASHES IN A FEMALE SUBJECT

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US); Jessica Engle, Ocala, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 82 days.

(21) Appl. No.: 15/582,802

(22) Filed: May 1, 2017

(65) Prior Publication Data
US 2017/0231950 A1    Aug. 17, 2017

Related U.S. Application Data

(62) Division of application No. 14/810,515, filed on Jul. 28, 2015, now Pat. No. 9,669,006.

(51) Int. Cl.
| | |
|---|---|
| *A61K 36/81* | (2006.01) |
| *A61K 36/48* | (2006.01) |
| *A61K 36/45* | (2006.01) |
| *A61K 31/365* | (2006.01) |
| *A61K 31/01* | (2006.01) |
| *A61K 31/404* | (2006.01) |
| *A61K 45/06* | (2006.01) |
| *A61K 31/05* | (2006.01) |
| *A61K 31/09* | (2006.01) |
| *A61K 31/12* | (2006.01) |
| *A61K 31/335* | (2006.01) |
| *A61K 31/34* | (2006.01) |
| *A61K 31/341* | (2006.01) |
| *A61K 31/355* | (2006.01) |
| *A61K 36/55* | (2006.01) |
| *A23L 33/105* | (2016.01) |
| *A23L 33/11* | (2016.01) |
| *A23L 33/00* | (2016.01) |
| *A61K 9/00* | (2006.01) |
| *A61K 9/48* | (2006.01) |

(52) U.S. Cl.
CPC .......... *A61K 31/365* (2013.01); *A23L 33/105* (2016.08); *A23L 33/11* (2016.08); *A23L 33/40* (2016.08); *A61K 9/0053* (2013.01); *A61K 9/48* (2013.01); *A61K 31/01* (2013.01); *A61K 31/05* (2013.01); *A61K 31/09* (2013.01); *A61K 31/12* (2013.01); *A61K 31/335* (2013.01); *A61K 31/34* (2013.01); *A61K 31/341* (2013.01); *A61K 31/355* (2013.01); *A61K 31/404* (2013.01); *A61K 36/45* (2013.01); *A61K 36/55* (2013.01); *A61K 36/81* (2013.01); *A61K 45/06* (2013.01); *A23V 2002/00* (2013.01)

(58) Field of Classification Search
CPC .......... A61K 36/81; A61K 36/48; A61K 36/45
USPC ......................... 424/757, 777, 758
See application file for complete search history.

(56) References Cited

U.S. PATENT DOCUMENTS

| | | | |
|---|---|---|---|
| 6,451,849 B1 | 9/2002 | Ahotupa et al. | |
| 6,613,792 B1 | 9/2003 | Ellenberger et al. | |
| 6,623,769 B1 | 9/2003 | Lorant et al. | |
| 8,460,718 B2 | 6/2013 | Zelkha et al. | |
| 8,669,293 B2 | 3/2014 | Levy et al. | |
| 9,000,049 B2 | 4/2015 | Manissier et al. | |
| 9,050,364 B2 | 6/2015 | Minatelli et al. | |
| 2001/0027216 A1 | 10/2001 | Levy et al. | |
| 2007/0010550 A1 | 1/2007 | McKenzie | |
| 2007/0269541 A1* | 11/2007 | Rohdewald | A61K 31/353 424/766 |
| 2007/0281998 A1 | 12/2007 | LaGuardia | |
| 2012/0121699 A1 | 5/2012 | Hsieh | |
| 2014/0120234 A1 | 5/2014 | Minatelli et al. | |
| 2017/0027904 A1 | 2/2017 | Minatelli et al. | |

FOREIGN PATENT DOCUMENTS

| | | |
|---|---|---|
| DE | 2002221672 | 2/2007 |
| WO | WO 2005107729 | 11/2005 |
| WO | WO2006072647 | 7/2006 |

OTHER PUBLICATIONS

Doshi et al. The Role of Oxidative Stress in Menopause, (Journal of Mid-Life Health, 2013, vol. 4, Issue 3, p. 140-146. (Year: 2013).*
Bewhole "FemCool—Cool down hot flashes, promote hormone balance, and support menopause & perimenopause Health", http://www.bewhole.com/femcool/, 2015, pp. 1-18.
Fern Cool Fact sheet, http://valensa.com/wp-content/uploads/2016/12/fem_cool_fact_sheet.pdf, Dec. 2016, 1 pg.
Triquetra Health, https://vimeo.com/162381542, "FemCool—Perimenopausal and Menopausal System Relief", Vimeo, Apr. 11, 2016 (video), https://vimeo.com, Triquetra Health, Videos, 1 pg fact sheet.
Sadler, "Soy and health 2006: clinical evidence—dietetic applications", British Nutrition Foundation, 2007, pp. 85-90.
Khajuria et al., "Dietary supplement in menopause", JK Science, Review Article, vol. 10, No. 1, Jan.-Mar. 2008, pp. 1-3.
Doshi et al, "The role of oxidative stress in menopause" Journal of Mid-Life Health, 2013, vol. 4, Issue 3, p. 140-146.

(Continued)

Primary Examiner — Christopher R Tate
Assistant Examiner — Deborah A Davis
(74) Attorney, Agent, or Firm — Allen, Dyer, Doppelt + Gilchrist, P.A.

(57) ABSTRACT

A dietary supplement composition is formulated in a therapeutic amount to treat and alleviate symptoms of hot flashes in a female subject, such as experiencing symptoms of perimenopause. The composition includes a phytoestrogen and lycopene in an oral dosage form. The phytoestrogen may include a plant lignan including at least one of Matairesinol, 7-hydroxymatairesinol, Secoisolariciresinol, Lariciresinol and Pinoresinol. The lycopene may include a lycopene complex having at least one of phytoene, phytofluene, beta-carotene, tocopherols and phytosterols.

26 Claims, No Drawings

(56) References Cited

OTHER PUBLICATIONS

Llanos et al. "Effects of Tomato and Soy on Serum Adipokine Concentrations in Postmenopausal Women at Increased Breast Cancer Risk: A Cross-Over Dietary Intervention Trial" J Clin Endocrinol Metab, Feb. 2014, 99(2):625-632.
Penalvo et al. "Dietary Sesamin is Converted to Enterolactone in Humans" The Jounal of Nutrition; pp. 1056-1062 http://jn.nutrition.org/content/135/5/1056.full.pdf+html?sid=086c6645-9acc-4280-805f-7e4cf4dc08a8 retrieved for internet Aug. 6, 2015.
Taku et al. "Extracted or synthesized soybean isoflavones reduce menopausal hot flash frequency and severity: systematic review and meta-analysis of randomized controlled trials" Menopause: The Journal of the North American Menopause Society vol. 19 No. 7; Jul. 2012; pp. 15.
Udani et al. "Pharmacokinetics and Bioavailabilty of Plant Lignan 7-Hydroxymatairesinol and Effects on Serum Enterolactone and Clinical Symptoms in Postmenopausal Women: A Single-Blinded, Parallel, Dose-Comparison Study" Journal of the American College of Nutrition, vol. 32, No. 6, 428-435 (2013).
"Lycopene" http://ww5.komen.org/breastcancer/lycopene.html: retrieved from internet Jun. 29, 2015; pp. 13.
"HMRIignan" Linnea SA informative document: Jan. 9, 2010; pp. 4.
Cunningham et al. "Molecular structure and enzymatic function of lycopene cyclase from *Cyanobadterium synechosoccus* sp strain PCC7942" The Plant Cell, vol. 6, 1107-1121: Aug. 1994.
Heinonen et al. "In Vitro Metabolism of Plant Lignans: New Precursors of Mammalian Lignans Enterolactone and Enterodiol" J. Agric. Food Chem. 2001, 49, 3178-3186.

\* cited by examiner

COMPOSITION AND METHOD TO TREAT AND ALLEVIATE SYMPTOMS OF HOT FLASHES IN A FEMALE SUBJECT

PRIORITY APPLICATION(S)

This is a divisional application based upon U.S. patent application Ser. No. 14/810,515 filed Jul. 28, 2015, the disclosure which is hereby incorporated by reference in its entirety.

FIELD OF THE INVENTION

The present invention relates to compositions and methods to treat and alleviate symptoms of menopause, and more particularly, this invention relates to a composition and method to treat and alleviate symptoms of hot flashes in a female subject such as experiencing symptoms of perimenopause.

BACKGROUND OF THE INVENTION

Menopause is defined as the period occurring 12 months after a woman's last menstrual cycle, and generally occurs in their 40's or 50's. The average age of menopause in women is about age 51. The process of menopause starts several years before, in a transition period called perimenopause. This is the time period where the ovaries gradually begin to make less estrogen. The symptoms of perimenopause can range from minor to extreme and usually is problematic for premenopausal women. Symptoms may include hot flashes, breast tenderness, lower sex drive, fatigue, irregular periods, vaginal dryness, urine leakage and urgency, mood swings and trouble sleeping. An estimated 6,000 women reach menopause every day (over 2 million per year) in the United States alone, and 75-85% of these women experience hot flashes and night sweats. Traditionally, women have been prescribed Hormone Replacement Therapy (HRT) to help with these symptoms. In recent years, several studies have shown that women taking HRT drugs have a higher risk of breast cancer, heart disease, stroke and blood clots. The largest study was the Women's Health Initiative (WHI), a 15-year study tracking over 161,800 healthy, postmenopausal women exploring the HRT therapy plus dietary modification and calcium supplementation. That study found that women who took the combination therapy with HRT had an increased risk of heart disease.

With disadvantages associated with Hormone Replacement Therapy, it is desirable if other supplements can be used to treat and alleviate symptoms of hot flashes in a female subject. Some women take phytoestrogens, which include enterolactone precursors such as HMR Lignans that contain 7-hydroxymatairesinol. These remedies have been around for a number of years and provide some relief, but further improvements are desired since many women will still suffer hot flash symptoms even when substantial dosages of the phytoestrogens such as HMR Lignan that contains the 7-hydroxymatairesinol are used. Therefore, even further improvements in remedies other than hormone replacement therapies for reducing hot flashes and other symptoms of perimenopause in women are desired.

SUMMARY OF THE INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

A dietary supplement composition is formulated in a therapeutic amount to treat and alleviate symptoms of hot flashes in a female subject. The composition comprises a phytoestrogen and lycopene in an oral dosage form. In an example, the female subject may be a female experiencing symptoms of perimenopause.

In another example, the phytoestrogen comprises a plant lignan including at least one of Matairesinol, 7-hydroxymatairesinol, Secoisolariciresinol, Lariciresinol, Pinoresinol, sesame seed oil, and sesamin. The composition may further comprise 10 to 50 mg of HRM Lignan as 7-hydroxymatairsterol, and in another example, 20 to 45 mg of HMR Lignan as 7-hydroxymatairsterol.

In another example, the phytoestrogen may comprise an enterolactone precursor. The lyocopene may comprise a lycopene complex comprising at least one of phytoene, phytofluene, beta-carotene, tocopherols and phytosterols. The composition may include 2 to 10 mg of lycopene, and in another example, 4 to 8 mg of lycopene. The composition may include 40 to 120 mg of Diindolymethane (DIM). The composition may include 40 to 80 mg of cranberry. The composition may include at least one of astaxanthin, zeaxanthin, lutein and xanthophylis.

In yet another example, a method of treating and alleviating symptoms of hot flashes in a female subject includes administering to the female subject in need thereof a therapeutic amount of a dietary supplement composition comprising a phytoestrogen and lycopene in an oral dosage form. The female subject may be a female experiencing symptoms of perimenopause.

The phytoestrogen may comprise a plant lignan including at least one of Matairesinol, 7-hydroxymatairesinol, Secoisolariciresinol, Lariciresinol and Pinoresinol. The method may include delivering 10 to 50 mg of HMR Lignans, including 7-hydroxymatairsterol. The method may include delivering 20 to 45 mg of HMR Lignans, including 7-hydroxymatairsterol. The phytoestrogen may comprise an enterolactone precursor.

The lycopene may comprise a lycopene complex comprising at least one of phytoene, phytofluene, beta-carotene, tocopherols and phytosterols. The method includes delivering 2 to 10 mg of lycopene. The method includes delivering 4 to 8 mg of lycopene. The dietary supplement composition may include 40 to 120 mg of Diindolymethane. The dietary supplement composition may include 40 to 80 mg of cranberry. The dietary supplement composition may include at least one of astaxanthin, zeaxanthin, lutein and xanthophylis.

DETAILED DESCRIPTION

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

A dietary supplement composition is formulated in a therapeutic amount to treat and alleviate symptoms of hot flashes in a female subject wherein the composition includes a phytoestrogen such as HMR Lignan (7-hydroxymatairsterol) and a carotenoid such as lycopene in an oral dosage form. This treatment and alleviation of the symptoms of hot flashes has been found especially beneficial in a female experiencing symptoms of perimenopause. In an example the phytoestrogen is a plant lignan, including at least one of Matairesinol, 7-hydroxymatairsterol, Secoisolariciresinol, Lariciresinol, Pinoresinol, sesame seed oil, or an isolated precursor sesamin contained in sesame seed oil. An example phytoestrogen includes HMR Lignan that contains 7-hydroxymatairsterol, and in an example, 10 to 50 mg of HMR Lignan as 7-hydroxymatairsterol and in another example, 20 to 45 mg of HMR Lignan as 7-hydroxymataieresinol.

In a clinical trial explained below, 36 mg of HMR Lignan was used and in another example, 20 mg was initially used. In the same clinical trial, the carotenoid such as lycopene was used. The lycopene could be formed as a lycopene complex that includes at least one of phytoene, phytofluene, beta-carotene, tocopherols and phytosterols. In an example, 2 to 10 mg of lycopene was used and in another example, 4 to 8 mg of lycopene was used. In a clinical trial explained below, either 8 or 4 mg of lycopene was used and in an example, 0 mg in order to determine the efficacy of the lycopene relative to the HMR Lignan and other components. The composition also included 40 to 120 mg of Diindolymethane (DIM) or 30 to 140 mg of Diindolymethane, and in an example, 50 milligrams of DIM was used in one trial and 100 milligrams in another trial. About 40 to 80 mg of cranberry was used and in an example, 60 milligrams of cranberry was used as cranberry powder, which gave the coloring and other benefits. Cranberry is used to help relieve adverse urinary symptoms and aid and treat urinary tract infections. Other carotenoids that may possibly be used include at least one of astaxanthin, zeaxanthin, lutein, and xanthophylis.

An explanation and results of the clinical trial are explained below.

A study was conducted to evaluate the effectiveness of a dietary supplement formulation on the reduction and severity of hot flashes in women. HMR Lignans (7-hydroxymatairesinol) were used and are naturally occurring phytoestrogens, derived from the Norway Spruce. Dietary lignans are converted to enterolactone (ENL), which mimics the effects of the estrogen hormone in humans. DIM (Diindolylmethane) is a compound derived from the digestion of indole-3-carbinol, found in cruciferous vegetables such as broccoli. DIM possesses a unique phytochemical constituent able to modify the metabolism of estrogen. Tomato Lycopene is a potent antioxidant naturally present in fruits and vegetables.

In this design, two female subjects experiencing symptoms of perimenopause, particularly hot flashes, were given a formula containing HMR Lignan as 7-hydroxymatairsterol, DIM (Diindolylmethane), lycopene, and cranberry juice powder. Female Subject 1 was 46-year-old female who was experiencing 3-4 severe hot flashes per day. The most severe hot flashes woke her at night with severe sweating. Female Subject 2 was a 50-year-old female who experienced 9-12 hot flashes throughout the day, which ranged from mild to severe. The most severe usually occurred in the afternoon and evening. Each woman was given a 30 day count bottle of the capsules to be taken once per day with water.

| TRIAL A-Given to both Female Subject One and Two | |
|---|---|
| Fill Ingredient | Mg Active |
| Cranberry Powder | 60.0 |
| Lycopene 20% VegBead | 8.0 |
| DIM | 100.0 |
| HMR Lignan | 20.0 |

Result: By day 2, both female subjects were free of both hot flashes and night sweats.

For reduction of formula dose cost, the formula was altered in two different ways, and given to each female subject. Trial B was the same formula as Trial A with the absence of lycopene and trial C was the same formula with 50% less DIM. HMR was raised to 36 mg.

| TRIAL B-Given to Female Subject One | |
|---|---|
| Fill Ingredient | mg Active |
| Cranberry Powder | 60.0 |
| Lycopene 20% VegBead | 0.0 |
| DIM | 100.0 |
| HMR Lignan | 36.0 |

| TRIAL C-Given to female Subject Two | |
|---|---|
| Fill Ingredient | mg Active |
| Cranberry Powder | 60.0 |
| Lycopene 20% VegBead | 8.0 |
| DIM | 50.0 |
| HMR Lignan | 36.0 |

Result: TRIAL B: After 3 days, Female Subject One started to get what she described as mini-hot flashes. The frequency was similar to what she was experiencing before treatment, but the severity was about 50% reduced. TRIAL C: Female Subject Two remained hot flash free even after the reduction of the DIM.

As a follow up to Trial B and C, one new formula was developed to be given to Female Subject One with the same formula as Trial A, but with 50% reduction of lycopene.

| TRIAL D-Given to Female Subject One | |
|---|---|
| Fill Ingredient | mg Active |
| Cranberry Powder | 60.0 |
| Lycopene 20% VegBead | 4.0 |
| DIM | 100.0 |
| HMR Lignan | 36.0 |

Result: After two days, woman one's hot flashes that were occurring while on Trial B were completely eliminated by the reintroduction of lycopene.

For reduction of cost, Trial E was developed with the same formula as Trial D, but with 50% less DIM.

| TRIAL E-Given to Female Subject One | |
|---|---|
| Fill Ingredient | mg Active |
| Cranberry Powder | 60.0 |
| Lycopene 20% VegBead | 4.0 |
| DIM | 50.0 |
| HMR Lignan | 36.0 |

| TRIAL F-Given to Female Subject One | |
|---|---|
| Fill Ingredient | mg Active |
| Cranberry Powder | 60.0 |
| Lycopene 20% VegBead | 4.0 |

| TRIAL F-Given to Female Subject One | |
|---|---|
| Fill Ingredient | mg Active |
| DIM | 0.0 |
| HMR Lignan | 36.0 |

Result: Female Subject One remained hot flash free for both Trial E and Trial F. There were no side effects or adverse reactions reported during the trials.

| TRIAL G-Given to Female Subject One | |
|---|---|
| Fill Ingredient | mg Active |
| Cranberry Powder | 60.0 |
| Lycopene 20% VegBead | 4.0 |
| DIM | 50.0 |
| HMR Lignan | 0.0 |

| TRIAL H-To Be Given to Female Subject One (Pending) | |
|---|---|
| Fill Ingredient | mg Active |
| Cranberry Powder | 0.0 |
| Lycopene 20% VegBead | 4.0 |
| DIM | 50.0 |
| HMR Lignan | 36.0 |

In summary, it was concluded that lycopene in combination with HMR Lignan reduces both the frequency and severity of hot flashes.

Trial formula G was given to female subject one, and within 4 days the female subject started experiencing hot flashes. There was a 20% reduction in severity, and 25% reduction in the frequency of hot flashes compared to severity and frequency prior to the trials. The subject remained on the trial for 2 weeks, and switched back to trial E formula and the hot flashes ceased after 2 days.

At this point in the trial it appears that both lycopene and HMR lignans work alone to control hot flashes, but have optimum performance when used together.

Trial H will be done to rule out the effect of cranberry powder on the results.

| Trial Summary | | | | | | |
|---|---|---|---|---|---|---|
| | Active Ingredient (mg) | | | | Reported Hot Flashes | |
| Trial | Lycopene | HMR Lignan | DIM | Cranberry Juice Powder | Subject 1 | Subject 2 |
| A | 8 | 20 | 100 | 60 | 100% Reduction in frequency and severity | 100% Reduction in frequency and severity |
| B | 0 | 36 | 100 | 60 | 0% Reduction in frequency, 60% reduction in severity | Not Tested |
| C | 8 | 36 | 50 | 60 | Not Tested | 100% Reduction in frequency and severity |
| D | 4 | 36 | 100 | 60 | 100% Reduction in frequency and severity | Not Tested |
| E | 4 | 36 | 50 | 60 | 100% Reduction in frequency and severity | Not Tested |
| F | 4 | 36 | 0 | 60 | 100% Reduction in frequency and severity | Not Tested |
| G | 4 | 0 | 50 | 60 | 20% reduction in severity and 25% reduction in frequency | Not Tested |
| H | 4 | 36 | 50 | 0 | Pending | |

The composition containing the HRM lignan and carotenoid as lycopene is advantageous over HRM lignan alone and did not appear to have adverse side effects associated with some prescription medications some users take such as covaryx, estratest H.S., EEMT HS, and syntest DS. These are esterified estrogens and methyltestosterones used to treat symptoms of menopause, including hot flashes, vaginal dryness, burning and irritation. These types of prescription medications as esterified estrogens and methyltestosterones increase the risk of developing endometrial hyperplasia, a condition that may lead to cancer of the uterus. Taking progestens while using esterified estrogens and methyltestosterones, however, may lower this risk. It is known that the long term use of esterified estrogens and methyltestosterone treatments may increase the risk of breast cancer, heart attack or stroke. The clinical trial described above shows the benefits when using phytoestrogens and lycopene.

Different types of phytoestrogens may be used, including the lignans listed below in Table 1 and coumesterol as found in red clover, soybeans, brussel sprouts, spinach, and some legumes. Other phytoestrogens may include phenylflavonoids such as erythrina burttii bark, and isoflavonoids such as soy and red clover. HRM lignans are from Norway spruce and possible other lignans that may be used from other foods are listed below in Table 1.

TABLE 1

| | secoisolariciresinol mg/100 g | matairesinol mg/100 g | Note |
|---|---|---|---|
| Flaxseed | 350 | 1 | Seco as glycoside |
| Rye, Wheat, Oat, Barley | 0.05-0.1 | 0-0.1 | Whole grain products |
| Cranberry Strawberry | | trace | |
| Peanuts, hazelnuts, cashew nuts, pistachio nuts | | trace | |
| Tea (different varieties) | 1-1.25 | trace | |

TABLE 1-continued

| | secoisolariciresinol mg/100 g | matairesinol mg/100 g | Note |
|---|---|---|---|
| Soy (different varieties | 0.2-1 | trace | |
| HMR Lignan ™ | | 80,000 | As 7-hydroxyl-matairesinol |

There now follows examples in greater detail for the phytoestrogens and carotenoids such as lycopene and other ingredients that may be used in the composition and method for alleviating and treating symptoms of hot flashes.

Examples of phytoestrogens include plant lignans that when ingested are converted into "human lignans" as primarily enterolactone that exerts estrogen-like activity. Known dietary sources of enterolactone precursors include flaxseed and sesame seed. Of course, because the amount of enterolactone produced depends on the person's gut microbiota, different amounts will be produced by different people depending on different factors, including physiology. The enterolactone will bind weakly to estrogen receptors and block overt estrogen activity in specific selected tissues. It may also stimulate the synthesis and circulating levels of Sex Hormone-Binding Globulin (SHBG). Thus, it may reduce the free bioavailable pool of circulating estrogen and reduce estrogen penetration in tissues and diminish the risk for adverse estrogen balance. It may also inhibit biosynthesis of estrogen by blocking aromatase as a key enzyme in the biosynthesis of estradiol.

Many of the phytoestrogens have a structural similarity with the estradiol (17-β-estradiol) and cause the estrogenic and/or anti-estrogenic effects by sitting in and blocking the receptor sites against estrogen. Thus, they can mildly mimic and sometimes operate as an antagonist of estrogen. Many phytoestrogens belong to the group of substituted natural phenolic compounds as the coumestans, prenylflavonoids, and isoflavones. Some phytoestrogens have a higher affinity for one variant of the estrogen receptor such as ER-β compared to ER-α. The structure of the phytoestrogens usually include the phenolic ring to bind to the estrogen receptor and a ring of isoflavones that mimic a ring of estrogen at the receptor binding site and include the lower molecular weight similar to estrogen, e.g., around 272. The distance between the hydroxyl group at the nucleus of the isoflavones is similar to that of estradiol and there is an optimal hydroxylation pattern.

Different food sources may contain some phytoestrogens that can be derived from those feed sources. Examples include soybeans and soy products, linseed as flax oil, oats, barley, beans, wheat berries, tempeh, fenugreek, lentils, alfalfa, rice, yams, mung beans, wheat germ, pomegranates, lupin, rice bran, apples, carrots, bourbon, hops, coffee, licorice root, ginseng, mint, kudzu, beer, red clover, anise, and fennel. Sesamin is a lignan that is isolated from the bark of fagara plants and derived from sesame oil and has a major metabolyte as the enteralactone with an elimination half life of less than 6 hours. Isoflavones are naturally occurring isoflavonoids that may be used to produce the phytoestrogens and also enhance antioxidant activity to trap singlet oxygen. They are found typically in the bean family. Soy isoflavones have been found advantageous as well as Genistein and daidzein that grow estrogen-receptor positive and negative breast cancer cells in vitro.

The clinical trial study explained above used the HMR Lignans, which are derived from the Norway Spruce and contain 7-hydroxymatairsterol, a known phytoestrogen. It is the direct metabolic precursor of the mammalian lignan, enterlactone. Human intestinal flora converts HRR lignan into enterolactone, acting as an enterolactone precursor. This conversion takes place in the intestines and thus readily absorbed into blood plasma.

The enteralactone then mimics the effects of the estrogen hormone without its common side effects. A 2002 Canadian investigated flaxseed dietary supplement (a weaker 7-hydroxymatairsterol enterolactone precursor), versus hormone replacement therapy in hypercholesterolemic menopausal women. The flaxseed was shown to improve mild menopausal symptoms.

Enterolactone has also been shown to inhibit aromatase activity, which increases the ratio of 2-hydroxyestrone to 16-alpha-hydroxyestrone in female urine. This aromatase inhibition therefore modulates the amount of estradiol in circulation by down-regulating its bio-availability to support estradiol dependent breast cancer cell proliferation. A recent study has shown that postmenopausal women with breast cancer have a significantly lower amount of the weaker 2-OH estrogen versus the 16a-OH estrogen compared to postmenopausal women without breast cancer. Postmenopausal women with higher levels of the 16a-OH estrogen in their bodies may be at higher risk for developing breast cancer. This study shows that while lignans work to modulate estrogen levels, it also works to modulate the estradiol (higher risk) which may reduce the chance of developing breast cancer. This is the opposite of the common HRT.

HMR Lignan may be standardized to deliver 800 mg/gram of lignans which compares favorably to unrefined flaxseed, which contains less than 50% of the lignan precursors available in HMR Lignan. It is estimated a user would have to take 20-30 grams of unrefined flaxseed each day to obtain the same benefit in menopausal symptom relief and hot flash reduction derived from 10-30 mg of HMR Lignan.

A single-blind parallel pharmakinetic and dose-comparison study had been conducted on 22 post-menopausal females who were not receiving hormone replacement therapy. With a 36 mg per day dose of HMR Lignan there was a 50% reduction in hot flashes through 8 weeks.

At doses as low as 10 mg/day, HMR Lignan produced a marked elevation in enterolactone concentration in plasma while well designed studies highlight the safety of this product and, unlike flaxseed, contains no secoisolariciresinol as the precursor of enterodiol. Some studies have been accomplished for in vitro metabolism of plant lignans and found new precursors of mammalian lignans enterolactone and enterodiol. One study allowed the quantitative analysis of lignan precursors and the mammalian lignans enterolactone and enterodiol by HPLC with a coulometric electrode array detector. The metabolic products, including mammalian lignans, were characterized as trimethylsilyl derivatives by gas chromatography-mass spectrometry. Most notable examples were matairesinol, secoisolariciresinol, pinoresinol, also known as pinoresinol diglucoside, lariciresinol, and 7-hydroxymatairesinol. Other compounds included syringaresinol diglucoside, arctigenin glucoside, and isolariciresinol.

DIM (Diindolymethane) was included in the clinical trial. DIM is derived from the digestion of indole-3-carbinol, which is found in cruciferous veggies such as broccoli, brussel sprouts, cabbage and kale. DIM may increase adaptive responses by regulating hormone metabolism, particularly estrogen. It may also convert the stronger estradiol, not a weaker form of estrogen, and may increase the metabolism of 2-hydroxy estrogens.

DIM has been shown to exert anti-carcinogenic effects in many experimental animal models and in human breast cancer cell lines with no tumor induction at high doses in any cell line. A great deal of research has been and continues to determine the exact mechanism associated with the unusual activity of DIM. The National Cancer Institute is also supporting clinical trials on DIM to determine if the product can be used as an adjunct therapy to prevent the further spread of the disease in breast cancer patients. This makes it an ideal ingredient in a menopause relief product.

Although lycopene is preferred, other carotenoids may be used in combination such as astaxanthin, zeaxanthin, lutein, and xanthophylis as described above. The mechanism why the carotenoid as lycopene in combination with a phytoestrogen such as HMR Lignans will give greater results for treating and alleviating symptoms of hot flashes is not known for certainty. Lycopene is a phytochemical found in tomatoes and other red fruits and vegetables, including carrots, watermelons, gak, and papayas. Although it is a carotene, it has no vitamin A activity. Some of its ability to work to reduce hot flashes may be due to its structure as a tetraterpene as formed from eight isoprene units. It is insoluble in water in part due to its 11 conjugated double bonds. In its all-trans form, the molecule is long and straight and constrained by its system of 11 conjugated double bonds. Thus, the energy required for electrons to transition to higher energy states is reduced because of the extension in that conjugated system. The lycopene as used in the clinical trial included a lycopene complex that included at least one of phytoene, phytofluene, beta-carotene, tocopherols, and phytosterols. It is possible that some of these components also enhanced the effect of reducing hot flashes in combination with the phytoestrogen.

Lycopene has been used for numerous treatments, such as to treat heart disease, enlarged prostate, and treat cancer. Lycopene has been used in combination with B-carotene and lutein to lower endogenous DNA damage than at baseline and is evidenced by decreased urinary excretion of 8-hydroxydioxoguanosine (8-OHdG).

Lycopene has been found more potent that alpha or beta-carotene respectively in inhibiting the proliferation of endometrial, breast and lung cancer cell lines. Studies further indicate in vitro in human prostate cancer cells that only lycopene among these same carotenoids is able to prevent progression of tumorogenesis.

Lycopene may modulate the deleterious mutations of hereditary BRCA1 or BRCA2 from conferring its normal high lifetime risk of developing breast cancer by decreasing DNA damage or by enhancing DNA repair and concluded that the prevention of hereditary breast cancer through diet is an attractive complement to the current management strategies.

Lycopene and retinoic acid inhibit insulin growth factor (IGF-1) induced proliferation of estrogen sensitive human breast and endometrial cancer cells during cell cycle progression in the G0/G1 growth phase and is dependent on Cyclin D1 levels. These results suggest that attenuation of Cyclin D1 levels by lycopene is an important mechanism for the reduction of the mitogenic action of IGF-1.

It is well known that 17-B-estradiol (E2) as well as the soy based phytoestrogen Genistein are both important risk factors for breast cancer. Lycopene may inhibit breast and endometrial cancer cell proliferation induced by either E2 or Genistein even in the presence of four different co-activators of estrogen response element (ERE) hormone stimulated reporter gene activity (ERE). These results suggest that dietary lycopene may inhibit estrogen signaling of both E2 or Genistein by attenuating their deleterious effect in hormone-dependent malignancies.

A cell-line specific modulation of breast cells by up-regulation on cell apoptosis, cell cycle and DNA repair mechanisms by lycopene occurred according to estrogen and retinoic acid receptor status.

The mechanistic work of lycopene is still to be determined to understand how lycopene exerts its clearly established down regulation of breast cancer cell proliferation and apoptosis. Emerging science strongly suggests that dietary intake of lycopene may be recommended for all women and in particular those with familial histories of breast cancer.

The use of lycopene enhances the effect to treat and alleviate symptoms of hot flashes in a female subject and in combination with the phytoestrogens gives a surprising result that those skilled in the art would not foresee. It is possible to use lycopene alone such as from 2 to about 10 milligrams a day, in one example, and in another example, 4 to 8 milligrams a day to help reduce the symptoms of hot flashes. Further studies are ongoing.

As noted before, 40 to 80 mg of cranberry may be used. In the clinical trial, 60 mg of cranberry was used in combination with other components. Cranberry gives the effective coloring that women have been found to associate with some positive female dietary supplements and gives the phytochemicals and polyphenols that are beneficial on the cardiovascular system and immune system and for and cancer prevention, while providing an abundant source of proanthocyanidins, flavonols, and quercetin. The cranberry may for some women alleviate problems associated with urinary tract infections. The cranberry can be a cranberry powder or other derivative.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A dietary supplement composition formulated in a therapeutic effective amount to treat and alleviate symptoms of hot flashes in a female subject experiencing symptoms of perimenopause comprising 10 to 50 mg of a plant lignan that contains 7-hydroxymatairesinol (HMR Lignan), 2 to 10 mg of lycopene, and 40 to 80 mg of cranberry powder in an oral dosage form, wherein said dietary supplement composition is in the form of a single dosage capsule.

2. The composition according to claim 1, wherein the composition further includes an additional plant lignan selected from the group consisting of Matairesinol, Secoisolariciresinol, Lariciresinol, Pinoresinol, sesame seed oil, and sesamin.

3. The composition according to claim 1, wherein the HMR Lignan is in an amount of 20 to 45 mg.

4. The composition according to claim 1, wherein the composition further includes a phytoestrogen that contains an enterolactone precursor.

5. The composition according to claim 1, wherein the lycopene is within a lycopene complex that further includes at least one of pytoene, plytofluene, beta-caratone, tocopherols, and phytosterols.

6. The composition according to claim 1, wherein the lycopene is in an amount of 4 to 8 mg.

7. The composition according to claim 1, wherein the composition further includes 40 to 120 mg of Diindolymethane.

8. The composition according to claim 1, wherein the dietary supplement composition further includes at least one of astaxanthin, zeaxanthin, lutein and xanthophylis.

9. The composition according to claim 1, wherein the amount of the lycopene is about 8 mg.

10. The composition according to claim 1, wherein the amount of the lycopene is about 4 mg.

11. The composition according to claim 1, wherein the amount of the HMR Lignan is about 20 mg.

12. The composition according to claim 1, wherein the amount of the HMR Lignan is about 36 mg.

13. The composition according to claim 1, wherein the amount of the cranberry powder is about 60 mg.

14. The composition according to claim 1, wherein the dietary supplement composition further comprises about 50 mg of Diindolymethane.

15. The composition according to claim 1, wherein the composition further comprises about 100 mg of Diinodolymethane.

16. A dietary supplement composition formulated in a therapeutic effective amount to treat and alleviate symptoms of hot flashes in a female subject experiencing symptoms of perimenopause comprising 10 to 50 mg of HMR lignan, 2 to 10 mg of lycopene, 40 to 80 mg of cranberry powder, and 40 to 120 mg of Diindolymethane in an oral dosage form, wherein said dietary supplement composition is in capsule form.

17. The composition according to claim 16, wherein the composition further includes a phytoestrogen that contains an enterolactone precursor.

18. The composition according to claim 16, wherein the lycopene is within a lycopene complex that further includes at least one of pytoene, plytofluene, beta-caratone, tocopherols, and phytosterols.

19. The composition according to claim 16, wherein the composition further includes at least one of astaxanthin, zeaxanthin, lutein and xanthophylis.

20. The composition according to claim 16, wherein the amount of the lycopene is about 8 mg.

21. The composition according to claim 16, wherein the amount of the lycopene is about 4 mg.

22. The composition according to claim 16, wherein the amount of the HMR Lignan is about 20 mg.

23. The composition according to claim 16, wherein the amount of the HMR Lignan is about 36 mg.

24. The composition according to claim 16, wherein the amount of the cranberry powder is about 60 mg.

25. The composition according to claim 16, wherein the amount of the Diindolymethane is about 50 mg.

26. The composition according to claim 16, wherein the amount of the Diindolymethane is about 100 mg.

* * * * *